(12) United States Patent
Inoue

(10) Patent No.: US 9,907,647 B2
(45) Date of Patent: Mar. 6, 2018

(54) INTRAOCULAR LENS INSERTION DEVICE AND METHOD FOR CONTROLLING MOVEMENT OF THE INTRAOCULAR LENS

(71) Applicant: Hoya Corporation, Tokyo (JP)

(72) Inventor: Masanobu Inoue, Honjo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 14/812,104

(22) Filed: Jul. 29, 2015

(65) Prior Publication Data

US 2016/0113759 A1    Apr. 28, 2016

Related U.S. Application Data

(63) Continuation of application No. 12/667,510, filed as application No. PCT/JP2008/062382 on Jul. 9, 2008, now Pat. No. 9,114,006.

(30) Foreign Application Priority Data

Jul. 11, 2007 (JP) ................................. 2007-182535

(51) Int. Cl.
*A61F 2/16* (2006.01)

(52) U.S. Cl.
CPC .................... *A61F 2/167* (2013.01)

(58) Field of Classification Search
CPC ................... A61F 2/167; A61F 2/1662; A61F 2002/1681; A61F 2002/1682
See application file for complete search history.

(56) References Cited

U.S. PATENT DOCUMENTS

| 2,761,446 A | 9/1956 | Reed |
| 4,205,747 A | 6/1980 | Gilliam et al. |
| 4,269,307 A | 5/1981 | LaHaye |

(Continued)

FOREIGN PATENT DOCUMENTS

| DE | 3610925 | 10/1987 |
| DE | 4110278 | 10/1992 |

(Continued)

OTHER PUBLICATIONS

U.S. Appl. No. 14/145,846, filed Dec. 31, 2013, U.S. 20140114323A1.

(Continued)

*Primary Examiner* — Gregory Anderson
*Assistant Examiner* — Sarah Simpson
(74) *Attorney, Agent, or Firm* — Henricks, Slavin & Holmes LLP

(57) ABSTRACT

Provided is an intraocular lens insertion device capable of omitting a repeated operation after the intraocular lens is inserted into the eye. The intraocular lens insertion device (1) comprises a lens setting part (11) for mounting an intraocular lens (5) having an optic (6) and one or two or more supporting portions (7a and 7b) disposed at the outer edge of the optic (6), a plunger (4) for pushing out the intraocular lens (5) mounted in the lens setting part (11), and a nozzle (13) for releasing the intraocular lens (5) pushed out by the plunger (4). This plunger (4) includes a lens contact portion (32) for abutting against the outer edge of the optic (6), and a pushing portion (33) for pushing out the supporting portion (7b) arranged in the backward direction of a lens advancing axis (A).

13 Claims, 6 Drawing Sheets

(56) References Cited

U.S. PATENT DOCUMENTS

| | | |
|---|---|---|
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A * | 9/1998 | Wolf ..................... A61F 2/167 606/107 |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 * | 6/2001 | Feingold ............... A61F 2/1664 606/107 |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,605,093 B1 | 8/2003 | Blake |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |

(56) References Cited

U.S. PATENT DOCUMENTS

| | | |
|---|---|---|
| 6,712,848 B1 | 3/2004 | Wolf et al. |
| 6,723,104 B2 | 4/2004 | Ott |
| 6,733,507 B2 | 5/2004 | McNicholas et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 9,289,288 B2 | 3/2016 | Someya et al. |
| 9,314,373 B2 | 4/2016 | Kudo et al. |
| 9,326,847 B2 | 5/2016 | Demas |
| 9,364,320 B2 | 6/2016 | Ichinohe et al. |
| 9,554,894 B2 | 1/2017 | Inoue |
| 9,572,710 B1 | 2/2017 | Kudo et al. |
| 9,655,718 B2 | 5/2017 | Kudo |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin et al. |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek et al. |
| 2006/0142781 A1 | 6/2006 | Pynson et al. |
| 2006/0167466 A1 | 7/2006 | Dusek |
| 2006/0200167 A1 | 9/2006 | Peterson et al. |
| 2006/0229633 A1 | 10/2006 | Shepherd |
| 2006/0235429 A1 | 10/2006 | Lee et al. |
| 2006/0293694 A1 | 12/2006 | Futamura |
| 2007/0005135 A1 | 1/2007 | Makker et al. |
| 2008/0033449 A1* | 2/2008 | Cole ............... A61F 2/1691 606/107 |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2010/0094309 A1 | 4/2010 | Hboukhny et al. |
| 2010/0106160 A1 | 4/2010 | Tsai |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2010/0331808 A1 | 12/2010 | Py et al. |
| 2011/0082463 A1 | 4/2011 | Inoue |
| 2011/0098717 A1 | 4/2011 | Inoue |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022549 A1 | 1/2012 | Someya et al. |
| 2012/0071887 A1 | 3/2012 | Ichinohe et al. |
| 2013/0006259 A1 | 1/2013 | Sanger |
| 2013/0018460 A1 | 1/2013 | Anderson |
| 2013/0226193 A1 | 8/2013 | Kudo et al. |
| 2013/0245635 A1 | 9/2013 | Inoue |
| 2014/0081284 A1 | 3/2014 | Ichinohe et al. |
| 2014/0107660 A1 | 4/2014 | Ichinohe et al. |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |
| 2016/0193038 A1 | 7/2016 | Kudo et al. |
| 2016/0346077 A1 | 12/2016 | Someya et al. |
| 2017/0079772 A1 | 3/2017 | Kudo |
| 2017/0151056 A1 | 6/2017 | Inoue |
| 2017/0202662 A1 | 7/2017 | Someya et al. |
| 2017/0252149 A1 | 9/2017 | Kudo et al. |
| 2017/0252150 A1 | 9/2017 | Kudo et al. |
| 2017/0258582 A1 | 9/2017 | Kudo et al. |

FOREIGN PATENT DOCUMENTS

| | | |
|---|---|---|
| EP | 0363213 | 4/1990 |
| EP | 0727966 | 9/2003 |
| EP | 1832247 A1 | 9/2007 |
| EP | 1338254 | 12/2008 |
| FR | 2749752 A | 12/1997 |
| JP | 63-197453 | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |

(56) References Cited

FOREIGN PATENT DOCUMENTS

| | | |
|---|---|---|
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| JP | 2014-050484 A | 3/2014 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO2002071982 A1 | 9/2002 |
| WO | WO2002096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |

OTHER PUBLICATIONS

U.S. Appl. No. 14/812,104, filed Jul. 29, 2015, U.S. 20160113759A1.

* cited by examiner

INTRAOCULAR LENS INSERTION DEVICE AND METHOD FOR CONTROLLING MOVEMENT OF THE INTRAOCULAR LENS

CROSS-REFERENCE TO RELATED APPLICATIONS

This application is a continuation of U.S. application Ser. No. 12/667,510, filed Dec. 31, 2009, now U.S. Pat. No. 9,114,006, which was the U.S. national phase under 35 U.S.C. § 371 of PCT International Application No. PCT/JP2008/062382, which has an International filing date of Jul. 9, 2008, and claims the benefit of Japanese Application No. 2007-182535, filed Jul. 11, 2007, each of which are incorporated by reference herein.

TECHNICAL FIELD

The present invention relates to an intraocular lens insertion device and a method for controlling movement of the intraocular lens used to implant an intraocular lens into an eye in place of a crystalline lens removed in cataract surgery.

BACKGROUND ART

In cataract surgery, there has been widely performed removal of opacified crystalline lenses by phacoemulsification and aspiration (PEA) followed by implantation of intraocular lenses into aphakic eyes. There are two types of intraocular lens: a hard intraocular lens whose optic is made of a hard material such as PMMA and a soft intraocular lens whose optic is made of a flexible material such as silicone elastomer, soft acrylic or hydrogel.

Upon use of a hard intraocular lens, the lens needs to be inserted through an incision having been cut in a cornea or sclera in a width approximately the same as the diameter of the optic of the lens. On the other hand, upon use of a soft intraocular lens, the lens can be inserted through an incision smaller than the diameter of the optic of the lens by folding the optic.

In order to reduce the risk of post-surgery corneal astigmatism or infection, insertion of a lens through a small incision is preferable. Consequently, soft intraocular lenses tend to be preferred now. There are three types of soft intraocular lens: Type 50 whose optic is made of a soft material and supporting portions are made of a hard material such as PMMA (generally, this type of intraocular lens has two thin filament-shaped supporting portions (FIG. 9A); Type 51 whose optic and supporting portions are made of the same soft material (generally, this type of intraocular lens has plate-like supporting portions (FIG. 9B); and Type 52 which has two or more thin plate-like supporting portions (FIG. 9C).

In addition, a dedicated intraocular lens insertion device having a mechanism to lead an intraocular lens to an eye through a slender tube is used in some cases in order to insert intraocular lenses into eyes. By using such an intraocular lens insertion device, an intraocular lens can be inserted through an incision opening smaller than 3 mm.

In recent years, in order to eliminate the possibility of bacterial contamination or operational error in handling intraocular lenses, an intraocular lens insertion device where an intraocular lens is set beforehand and which can be packaged and stored has been developed.

With such an intraocular lens insertion device, however, there was a problem that a supporting portion arranged in the backward direction of a lens advancing axis (hereinafter, referred to as a trailing supporting portion) got caught in the gap between a plunger for pushing out the intraocular lens and an inner wall of a passage of the insertion device or entangled in the plunger in a process of movement of the intraocular lens. Such a problem is brought to the fore especially with a soft intraocular lens having thin filament-shaped supporting portions or a soft intraocular lens having thin plate-like supporting portions.

In such an intraocular lens insertion device, if the trailing supporting portion stretches in a process of movement of the intraocular lens, the trailing supporting portion is left outside of the eye when the lens is inserted through a small incision in the eye. Therefore, after the lens is pushed by the plunger, a repeated operation for inserting the trailing supporting portion into the eye is required, and it takes time and labor in surgery. In some cases, while the intraocular lens is moving inside the intraocular lens insertion device, the optic and the trailing supporting portion interfere with each other, resulting in damage or breakage of the optic or the trailing supporting portion.

Therefore, when an intraocular lens is inserted into an eye using the intraocular lens insertion device, the behavior of the trailing supporting portion of intraocular lens needs to be controlled appropriately in a process of movement of the intraocular lens.

In view of the foregoing problems, a lens insertion tool which has a side clearance provided at the distal end of a plunger for accommodating a trailing supporting portion to prevent damage to the trailing supporting portion has been disclosed (Patent Document 1, for example). A lens insertion tool provided with a relief channel for a trailing supporting portion at the lower side of a plunger has been also disclosed (Patent Document 2, for example). Furthermore, a lens insertion tool wherein a plunger pushes a trailing supporting portion up a ramp and bends haptics up and over IOL has been disclosed (Patent Document 3, for example). Thus, the above-mentioned Patent Documents can reduce getting caught of a trailing supporting portion of intraocular lens having thin filament-shaped or plate-like supporting portions. Patent Document 1: Japanese Translation of PCT International Application No. 11-506357
Patent Document 2: U.S. Pat. No. 6,733,507
Patent Document 3: Japanese Unexamined Patent Publication No. 2004-351196

DISCLOSURE OF THE INVENTION

Problems to be Solved by the Invention

The above-mentioned Patent Documents 1 and 2, however, still have a problem that the trailing supporting portion relieved into a clearance at the distal end of plunger or a relief channel for a trailing supporting portion stretches and the trailing supporting portion is left outside of the incision when the intraocular lens is inserted through a small incision of the eye. Especially, an intraocular lens having thin plate-like supporting portions which are made of thick soft members has a problem that it takes time and labor to conduct a repeated operation. In the foregoing Patent Document 3, too, there are concerns that while an intraocular lens is moved further through the nozzle after the haptics are bent up and over IOL, the trailing supporting portion may be compressed into an unexpected shape, causing a breakage of the trailing supporting portion, a trouble during insertion, or a state of the folded trailing supporting portion accommodated in the intraocular lens not returning to a desired shape after insertion into an eye.

In view of the foregoing problems, an object of the present invention is to provide an intraocular lens insertion device and an intraocular lens movement control method which can appropriately control the behavior of a trailing supporting portion in a process of movement of the intraocular lens and can reduce the possibility of a repeated operation after insertion of the intraocular lens into an eye.

Means for Solving the Problems

The inventor of the present application conducted studies over and over again and found that the above-mentioned object could be achieved by folding an optic and supporting portions individually while minimizing the interference of the optic and the supporting portions during movement of the intraocular lens.

To achieve the above object, the invention according to claim 1 features an intraocular lens insertion device comprising: a lens setting part for setting an intraocular lens having an optic and one or two or more supporting portions disposed at the outer edge of the optic; a plunger for pushing out the intraocular lens set on the lens setting part; and a nozzle for releasing the intraocular lens pushed out by the plunger, the intraocular lens being set on the lens setting part with at least one of the supporting portions being arranged in the backward direction of a lens advancing axis, wherein the plunger includes a lens contact portion for abutting against the outer edge of the optic and a pushing portion for pushing out the supporting portion arranged in the backward direction of the lens advancing axis.

The invention according to claim 2 is characterized in that the pushing portion bends the supporting portion in the forward direction of the lens advancing axis.

The invention according to claim 3 is characterized in that the pushing portion bends the supporting portion in the forward direction of the lens advancing axis without interference of the optic and the supporting portion.

The invention according to claim 4 is characterized in that the pushing portion includes a guide extending in the direction of the lens advancing axis.

The invention according to claim 5 is characterized in that the pushing portion is a groove extending in the direction of the lens advancing axis.

The invention according to claim 6 is characterized in that the pushing portion includes a supporting portion abutting face for abutting against the deformed supporting portion.

The invention according to claim 7 features a method for controlling movement of an intraocular lens, comprising the steps of: setting an intraocular lens having an optic and one or two or more supporting portions disposed at the outer edge of the optic on a lens setting part with at least one of the supporting portions being arranged in the backward direction of a lens advancing axis; and moving the intraocular lens in the forward direction of the lens advancing axis, wherein the moving step includes the steps of: pushing out the supporting portion arranged in the backward direction of the lens advancing axis in the lens moving direction; and pushing out the outer edge of the optic in the forward direction of the lens advancing axis.

The invention according to claim 8 is characterized in that the step of pushing out of the supporting portion comprises a step of bending a tip of the supporting portion in the forward direction of the lens advancing axis.

Effect of the Invention

According to the intraocular lens insertion device set forth in claim 1 of the present invention, the pushing portion provided on the plunger moves an intraocular lens forward with the supporting portion being caught, thereby preventing the supporting portion from stretching backward as the intraocular lens is moving forward. Therefore, with this intraocular lens insertion device, the supporting portions can be inserted together with the optic into an eye through an incision at one operation, thereby omitting a repeated operation after the intraocular lens was inserted into the eye.

According to the intraocular lens insertion device set forth in claim 2 of the present invention, the optic and the supporting portion arranged in the backward direction of the lens advancing axis are prevented from being damaged or broken while the intraocular lens is moving.

According to the intraocular lens insertion device set forth in claim 3 of the present invention, the intraocular lens is moved forward with a minimum of interference of the optic and the supporting portion arranged in the backward direction of the lens advancing axis, thereby preventing the optic and the trailing supporting portion from being damaged or broken while the intraocular lens is moving.

According to the intraocular lens insertion device set forth in claim 4 of the present invention, the supporting portion arranged in the backward direction of the lens advancing axis is prevented from dropping off in a process of movement of the intraocular lens, resulting in a more reliable control of the supporting portion.

According to the intraocular lens insertion device set forth in claim 5 of the present invention, the supporting portion arranged in the backward direction of the lens advancing axis is pushed out by the supporting portion abutting face and can be inserted into the eye, thereby ensuring that a repeated operation after insertion of the lens into the eye can be omitted.

According to the intraocular lens insertion device set forth in claim 6 of the present invention, the supporting portion can be caught with a simple configuration.

According to the intraocular lens movement control method set forth in claim 7 of the present invention, the pushing portion provided on the plunger moves the intraocular lens forward with the supporting portion being caught, thereby preventing the supporting portion from stretching as the intraocular lens moves forward. Therefore, the intraocular lens insertion device enables the supporting portions to be inserted together with the optic into an eye through an incision at one operation. Thus, the intraocular lens insertion device can omit a repeated operation after insertion of the intraocular lens into the eye.

According to the intraocular lens movement control method set forth in claim 8 of the present invention, the supporting portion can be more surely prevented from stretching backward as the intraocular lens moves forward.

BRIEF DESCRIPTION OF THE DRAWINGS

FIG. 5A is a section view taken along line A-A in FIG. 5A'.

FIG. 5B is a section view taken along line B-B in FIG. 5B'.

FIG. 5C is a section view taken along line C-C in FIG. 5C'.

FIG. 6A is a section view taken along line A-A in FIG. 6A'.

FIG. 6B is a section view taken along line B-B in FIG. 6B'.

FIG. 6C is a section view taken along line C-C in FIG. 6C'.

BEST MODE FOR CARRYING OUT THE INVENTION

Hereinafter, a preferred embodiment of the present invention will be described with reference to the accompanying drawings.

1. Embodiment (1) General Structure

Figure 1:
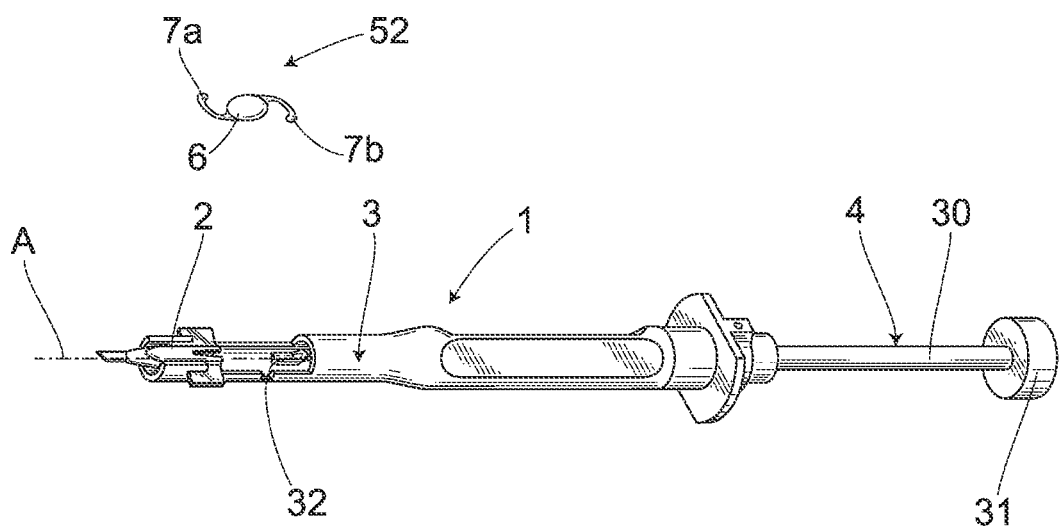
FIG. 1 shows the overall configuration of an intraocular lens insertion device of the present invention.

An intraocular lens insertion device 1 shown in FIG. 1 has a cartridge 2, a main body 3 and a plunger 4. The cartridge 2 is installed to the main body 3 after an intraocular lens 5 is set on the cartridge. On the other hand, the plunger 4 is provided so that it can move in the forward and backward directions of the lens advancing axis A inside the main body 3. The intraocular lens insertion device 1 having such a configuration is generally configured to push out the intraocular lens 5 set in the cartridge 2 by using the plunger 4 and to release the intraocular lens 5 from the end of the cartridge 2 into an eye.

For reference's sake, an intraocular lens insertion device 1 may be made of various materials. For example, synthetic resin may be used for all portions of the tool, thereby allowing easy mass production; or metal such as titanium may be used. The intraocular lens 5 also has an optic 6 and a pair of thin plate-like supporting portions (sometimes referred to as "loop haptics") 7a,7b disposed at the outer edge of the optic 6.

Hereinafter, each configuration will be described in detail. In the description below, the forward direction of the lens advancing axis A is simply referred to as "forward" and the backward direction of the lens advancing axis A is simply referred to as "backward".

Figure 2:
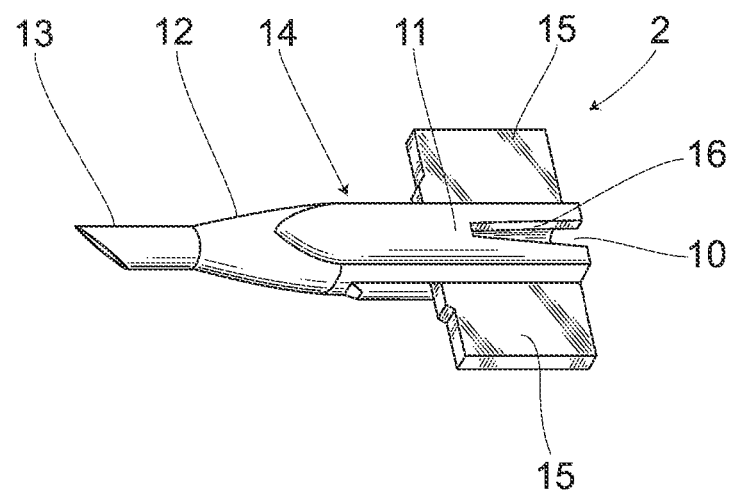
FIG. 2 is a perspective view showing the configuration of a cartridge of the same as above.

As shown in FIG. 2, the cartridge 2 comprises: a cartridge main body 14 having an insertion opening 10, a lens setting part 11, a transition part 12 and a nozzle 13 in the order along the lens advancing axis A; and wing portions 15,15 extending from both sides of the cartridge main body 14. At the insertion opening 10, an insertion groove 16 which was formed by notching in the direction of the lens advancing axis A is provided. In the forward direction of the lens advancing axis A of the insertion opening 10, a lens setting part 11 is provided. In the forward direction of the lens advancing axis A of the lens setting part 11, the transition part 12 is provided. The inner wall of the transition part 12 has a mortar shape tapering toward the distal end and communicates with a nozzle 13 at the distal end. With this configuration, the cartridge main body 14 is formed so that it can move from the lens setting part 11 to the transition part 12, and then, from the transition part 12 to the nozzle 13 when the intraocular lens 5 mounted on the lens setting part 11 through the insertion opening 10 is pushed by the plunger 4. The nozzle 13 is formed so that it has an outside diameter sized to be inserted into the incision opening (not shown). The bore of the cartridge 2 is formed so that it has an oval shape at the insertion opening 10, converging into a perfect circle toward the proximal end of the nozzle 13.

Figure 3:
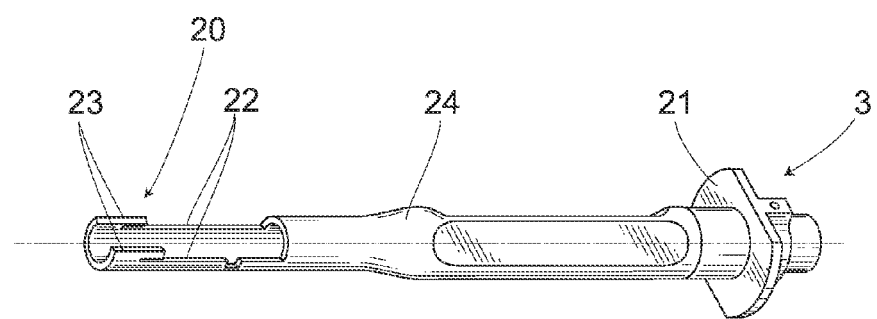
FIG. 3 is a perspective view showing the configuration of a main body of the same as above.

As shown in FIG. 3, the main body 3 comprises an attachment portion 20 for removably attaching the cartridge 2, a flange 21 for locking the fingers of the operator, and a tubular body 24 connecting the attachment portion 20 and the flange 21. The attachment portion 20 is provided at the distal end of the main body 3 formed into a semicircle shape and comprises guide passages 22,22 for guiding the wing portions 15,15 of the cartridge 2 and locking pieces 23,23 provided forward of the lens advancing axis A of the guide passages 22,22. The locking pieces 23,23 are configured so that it can lock the front ends of the wing portions 15,15 of the cartridge 2. The flange 21 is provided on the outer surface of the proximal end of the main body 3.

Next, a plunger 4 which is a characteristic component of the present invention will be described in detail. As shown in FIG. 1, the plunger 4 comprises a pushing rod 30 for pushing out the intraocular lens 5, a pressing portion 31 provided at the proximal end of the pushing rod 30 and a lens contact portion 32 provided at the distal end of the pushing rod 30. This plunger 4 is installed into the main body 3 in such a manner as to move forward or backward along the lens advancing axis A inside the main body 3. The plunger 4 installed into the main body 3 is configured so that the operator can push out the intraocular lens 5 by pushing the pressing portion 31 and bringing the lens contact portion 32 into contact with the intraocular lens 5 mounted on the lens setting part 11.

Figure 4:
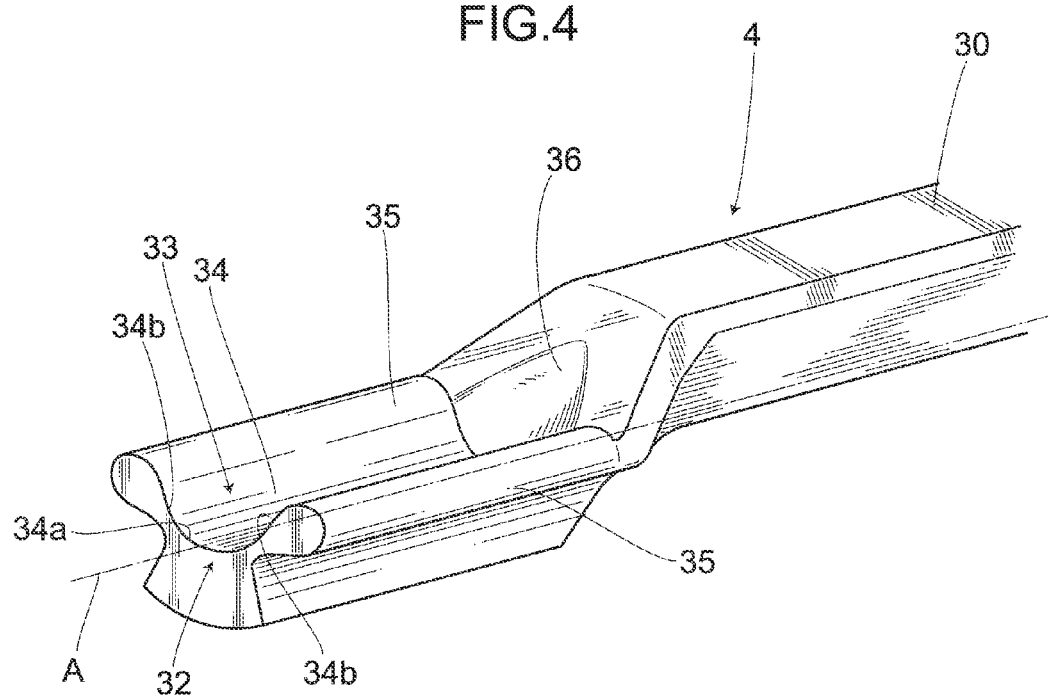
FIG. 4 is a partial perspective view showing the configuration of a plunger of the same as above.

As shown in FIG. 4, the plunger has a lens contact portion 32 and a pushing portion 33 connected to the lens contact portion 32 at the distal end of the pushing rod 30.

The lens contact portion 32 is formed by a vertical plane relative to the lens advancing axis A. The pushing portion 33 catches the supporting portion (hereinafter referred to as the trailing supporting portion) 7b arranged in the backward direction of the lens advancing axis A and moves the trailing supporting portion 7b together with the optic 6 without separating from the optic 6. The pushing portion 33 is provided on one side of the lens contact portion 32 and comprises a groove 34 extending in the backward direction from the distal end of the pushing rod 30, guides 35,35 provided on both sides of the groove 34 in parallel with the lens advancing axis A, and a supporting portion abutting face 36. In this embodiment, the groove 34 has a concave bottom face and connects to the guides 35,35 at the opening end of the side face 34b converging from the opening toward the bottom face 34a. These guides 35,35 are provided at both sides of the groove 34 and formed into a columnar shape, and their ends form part of the lens contact portion 32. The supporting portion abutting face 36 is provided so that a deformed trailing supporting portion 7b can abut against it. This supporting portion abutting face 36 is formed with a plane which slants backward as it goes upward from the surface of the groove 34, and blocks the backward end of the groove 34.

The plunger 4 having such a configuration is attached to the main body 3, as shown in FIG. 1, by inserting the lens contact portion 32, first, in the proximal end of the main body 3 and by positioning the lens contact portion 32 at the distal end of the main body 3 and the pressing portion 31 at the proximal end of the main body 3.

(2) Operation and Effect

Figure 5A:
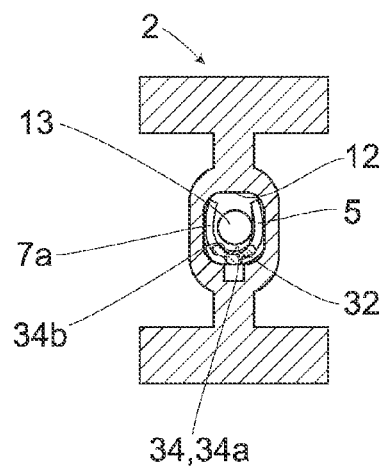
FIG. 5A' is a section view showing the intraocular lens insertion device illustrated in FIG. 1 with the plunger abutting against a supporting portion.
Figure 5A:
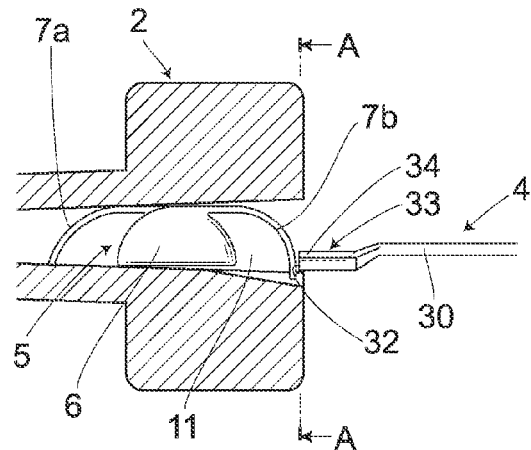
Figure 5B:
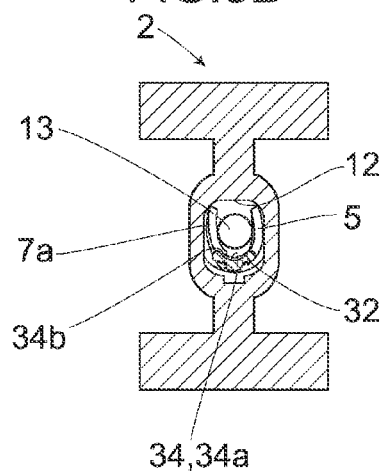
FIG. 5B' is a section view showing the intraocular lens insertion device illustrated in FIG. 1 with the plunger catching a supporting portion.
Figure 5B:
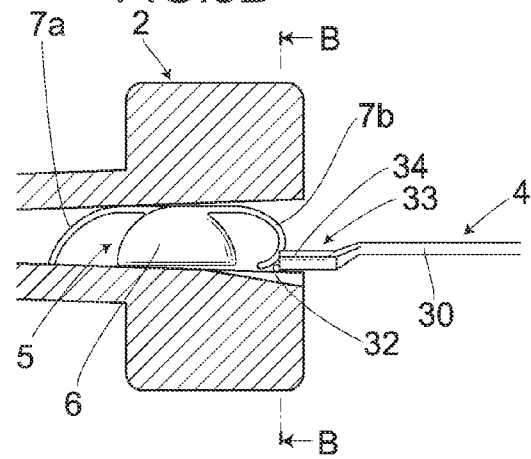
Figure 5C:
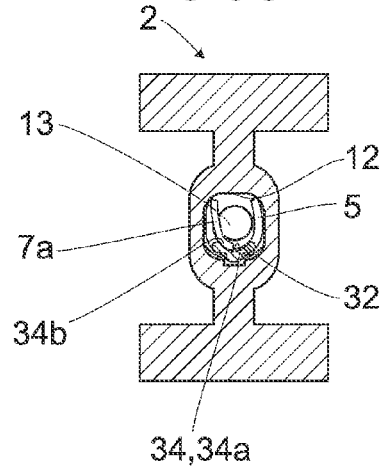
FIG. 5C' is a section view showing the intraocular lens insertion device illustrated in FIG. 1 with the plunger abutting against an optic.
Figure 5C:
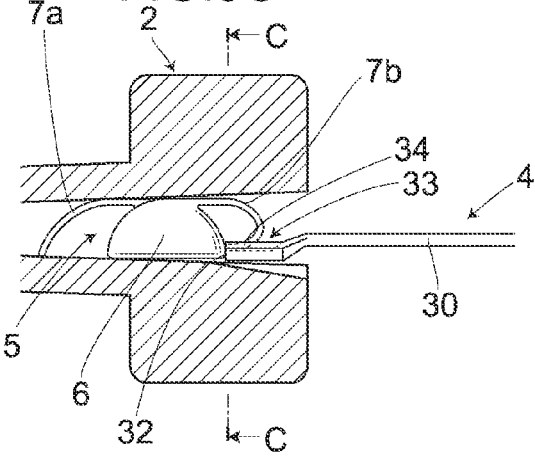

Next, the operation and effect of the above-mentioned intraocular lens insertion device 1 will be described with reference to the accompanying drawings. FIGS. 5A'-5C' are sectional views of the vicinity of the lens setting part 11 of the cartridge 2, and FIGS. 5A-5C are cross-sections of FIGS. 5A'-5C'.

First, the intraocular lens 5 folded into two by use of tweezers (not shown) is inserted through the insertion opening 10, and then the intraocular lens 5 is set on the lens setting part 11 of the cartridge 2 pre-filled with ophthalmic viscoelastic material. At this time, the intraocular lens 5 is set with a pair of supporting portions 7a,7b arranged in the forward and backward directions, respectively, relative to the optic 6 (FIGS. 5A and 5A'). The intraocular lens 5 is positioned with the folded optic 6 arranged on one side and the proximal ends of the supporting portions 7a,7b arranged on the other side, respectively. The tips of the supporting portions 7a,7b hang down on one side as they move in the forward and backward directions across the optic 6, respectively. Furthermore, the intraocular lens 5 which is folded into two comes into contact with the bore of the cartridge 2 formed into an oval shape, and accordingly, the supporting portions 7a,7b are arranged along the side wall of the bore.

Next, the cartridge 2 having the intraocular lens 5 mounted on the lens setting part 11 is attached to the attachment portion 20 of the main body 3 by sliding forward of the lens advancing axis A with the wing portions 15,15 mounted on the guide passages 22,22 and locking the front ends of the wing portions 15,15 with the locking pieces 23,23.

After the cartridge 2 is attached to the main body 3, the nozzle portion 13 is first inserted into an eye through the incision opening (not shown) by the operator.

On the other hand, the plunger 4 moves forward when the operator pushes the pressing portion 31. When the plunger 4 moves forward, the lens contact portion 32 provided at the distal end of the pushing rod 30 comes in contact with the tip of the trailing supporting portion 7b (FIGS. 5A and 5A'). At this time, the trailing supporting portion 7b is positioned along the bore of the cartridge 2 and comes in contact with the trailing supporting portion 7b at the distal end of the guides 35,35.

Furthermore, when the plunger 4 is pushed and the lens contact portion 32 moves forward, the trailing supporting portion 7b which is hanging down to one side is bent at its tip in the forward direction (FIGS. 5B and 5B'). At the same time, the trailing supporting portion 7b is guided into the central groove 34 by the side face 34b converging from the opening toward the bottom face 34a. In this way, the pushing portion 33 catches the trailing supporting portion 7b by supporting the tip of the trailing supporting portion 7b from one side by the groove 34.

The plunger 4, by which the trailing supporting portion 7b was caught at the pushing portion 33, is pushed further, and the lens contact portion 32 abuts against the outer edge of the intraocular lens 5 and moves the intraocular lens 5 forward (FIGS. 5C and 5C'). The intraocular lens 5 moving in the cartridge 2 is pushed inward by the inner wall of the transition part 12 and folded to a smaller size. In this way, the intraocular lens insertion device 1 releases the compactly folded intraocular lens 5 from the tip of the nozzle 13.

In the conventional intraocular lens insertion device 1, as the intraocular lens 5 moves forward, the trailing supporting portion 7b stretches backward. Therefore, by using the conventional intraocular lens insertion device 1, the trailing supporting portion 7b is left outside of the incision when the intraocular lens 5 is inserted through a small incision of an eye, and a repeated operation was needed to insert the trailing supporting portion 7b left outside of the incision into the incision.

In contrast, in the intraocular lens insertion device 1 according to this embodiment, the pushing portion 33 provided on the plunger 4 moves the intraocular lens 5 forward with the trailing supporting portion 7b being caught, thereby preventing the trailing supporting portion 7b from stretching backward as the intraocular lens 5 moves forward. Thus, the intraocular lens insertion device 1 allows the pushing portion 33 to move the intraocular lens 5 without separating the trailing supporting portion 7b from the optic 6 and enables the trailing supporting portion 7b and the optic 6 to be inserted into the eye through the incision at one operation. Therefore, the intraocular lens insertion device 1 can omit a repeated operation after the intraocular lens 5 was inserted into the eye.

In addition, the supporting portion abutting face 36 abuts against the trailing supporting portion 7b. By pushing out the trailing supporting portion 7b by the supporting portion abutting face 36, the trailing supporting portion 7b can be inserted into the eye. Thus, the intraocular lens insertion device 1 can omit a repeated operation more surely after the intraocular lens 5 was inserted into the eye.

As mentioned above, the plunger 4 is provided with a pushing portion 33 for pushing out the trailing supporting portion 7b, besides a lens contact portion 32, thereby folding the trailing supporting portion 7b and the optic 6, separately. Therefore, the intraocular lens insertion device 1 can move the intraocular lens 5 forward, keeping interference of the trailing supporting portion 7b and the optic 6 at a minimum level. Thus, the intraocular lens insertion device 1 can reduce interference of the optic 6 and the trailing supporting portion 7b during movement of the intraocular lens 5, thereby preventing the optic 6 and the trailing supporting portion 7b from being damaged or broken.

As mentioned above, in this embodiment, the guides 35,35 are formed into a columnar shape, and they can guide the trailing supporting portion 7b in contact with the distal ends of the guides 35,35 to the groove 34 without causing damage.

This pushing portion 33 is formed by the groove 34, thereby catching the trailing supporting portion 7b with such a simple structure. Also, the groove 34 has a concave bottom face and can guide the trailing supporting portion 7b in contact with the guides 35,35 smoothly in the groove 34 in the center.

In addition, the bottom face of the groove 34 on the pushing portion 33 is formed by a concave face, thereby catching the trailing supporting portion 7b guided to the groove 34 without causing damage.

Furthermore, as the pushing portion 33 is provided with the guides 35,35, it can prevent the caught trailing supporting portion 7b from falling off in the process of movement of the intraocular lens 5 and control the trailing supporting portion 7b with more reliability.

2. Modified Example of Cartridge

Figure 6A:
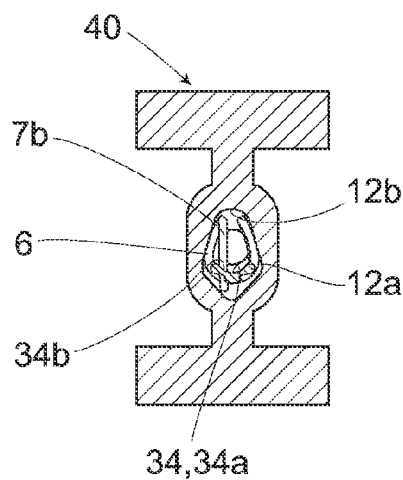
FIG. 6A' is a section view showing another exemplary intraocular lens insertion device with the plunger abutting against a supporting portion.
Figure 6A:
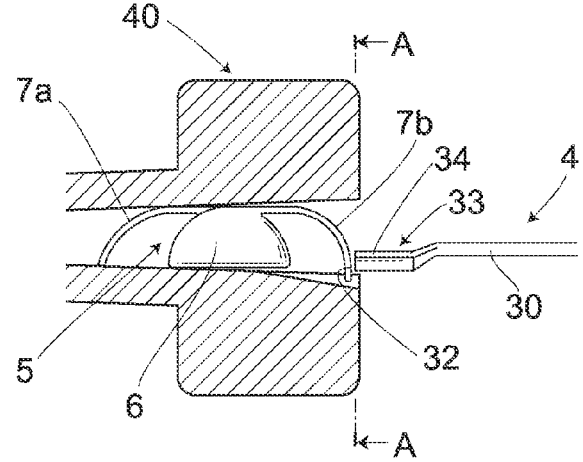
Figure 6B:
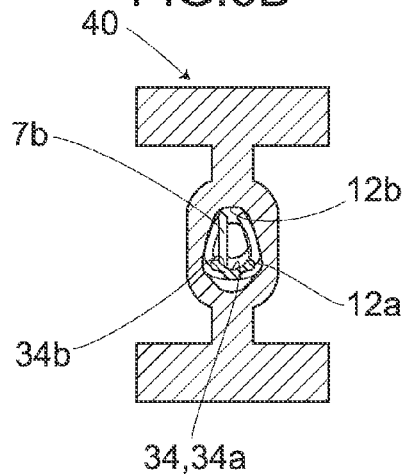
FIG. 6B' is a section view showing the intraocular lens insertion device illustrated in FIG. 6A' with the plunger catching a supporting portion.
Figure 6B:
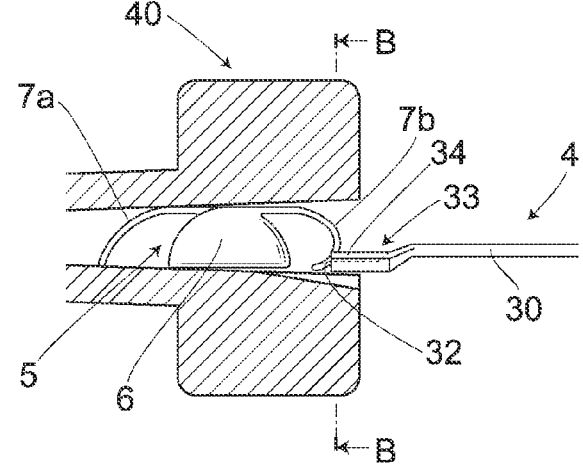
Figure 6C:
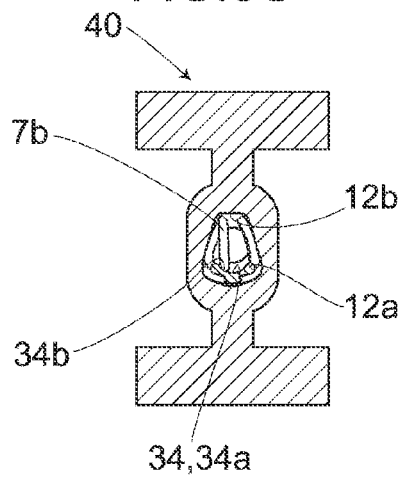
FIG. 6C' is a section view showing the intraocular lens insertion device illustrated in FIG. 6A' with the plunger abutting against an optic.
Figure 6C:
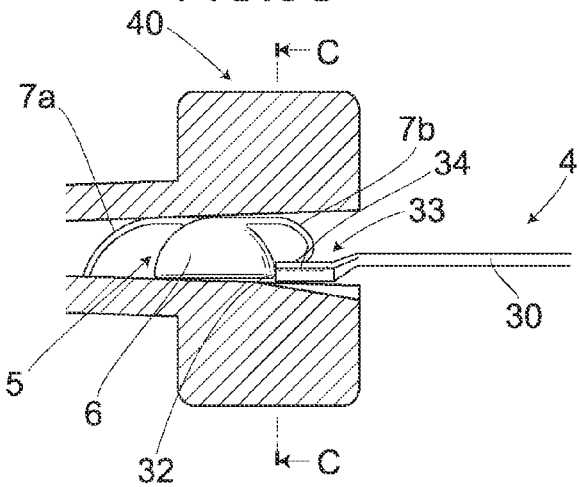

The difference between the cartridge 40 shown in FIGS. 6A-6C' and the above embodiment lies in only the bore shape. With regard to this cartridge 40, when the side of the bore where the optic 6 of the intraocular lens 5 folded into two is placed is regarded as one side 12a, the other side 12b has a smaller width compared to the one side 12a. FIGS. 6A'-6C' are sectional views of the vicinity of the lens setting part 11 on the cartridge 40 and FIGS. 6A-6C are cross-sections of FIGS. 6A'-6C'.

In this modified example, when the operator pushes the pressing portion 31, the plunger 4 moves forward and the lens contact portion 32 provided at the distal end of the pushing rod 30 abuts against the tip of the trailing supporting portion 7b (FIGS. 6A and 6A'). The trailing supporting portion 7b is pushed by the inner wall of the other side 12b in the bore of the cartridge 40 having a smaller width compared with the one side 12a which is the side of the optic 6 of the intraocular lens 5 placed on the cartridge and is placed in the vicinity of the center of the bore. As a result, the trailing supporting portion 7b comes in contact with the center of the pushing portion 33, that is, the groove 34.

When the plunger 4 is pushed further and the lens contact portion 32 moves forward, the trailing supporting portion 7b hanging down to the one side 12a is bent in the forward direction at its tip (FIGS. 6B and 6B'). At the same time, the trailing supporting portion 7b is guided into the groove 34 in the center by the side face 34b converging from the opening toward the bottom face 34a. In this way, the pushing portion 33 catches the trailing supporting portion 7b by supporting the tip of the trailing supporting portion 7b from the one side 12a by the groove 34.

When the plunger 4 which caught the trailing supporting portion 7b at the pushing portion 33 is further pushed, the lens contact portion 32 abuts against the outer edge of the intraocular lens 5 and the intraocular lens 5 is moved forward (FIGS. 6C and 6C'). In this way, the cartridge 40 according to this modified example has a bore whose width of the other side 2b is smaller than that of the one side 12a, allowing the trailing supporting portion 7b to be guided to the groove 34 in the center more easily than the above embodiment.

3. Modified Example of Plunger

Figure 7:
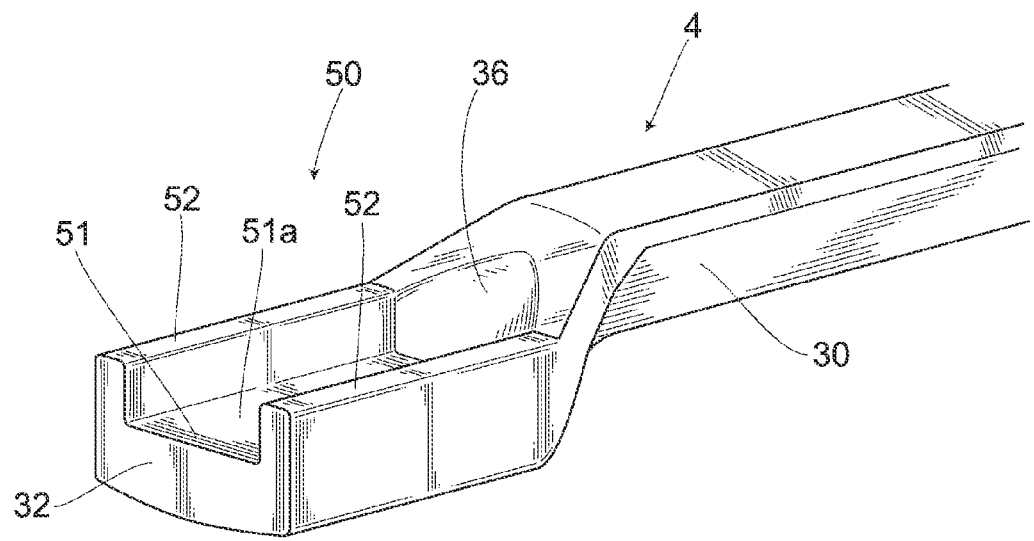
FIG. 7 is a view showing a modified example of a plunger of the same as above.

The plunger 4 shown in FIG. 7 is different from the above embodiment in the structure of a pushing portion. More specifically, the pushing portion 50 according to this modified example is formed into a rectangular parallelepiped shape defined by a groove 51 and guides 52,52 integrally set up on both sides of the groove 34. The distal ends of the guides 52,52 form part of the lens contact portion 32. The bottom face 51a of the groove 51 is formed by a flat plane, and a pair of guides 52,52 formed on both sides of the groove 51 have a rectangular parallelepiped shape. The corners of these guides 52,52 are processed into round shape. Though this modified example has a simple shape compared to the above embodiment, it has an effect of omitting a repeated operation after the intraocular lens 5 was inserted into an eye.

Figure 8:
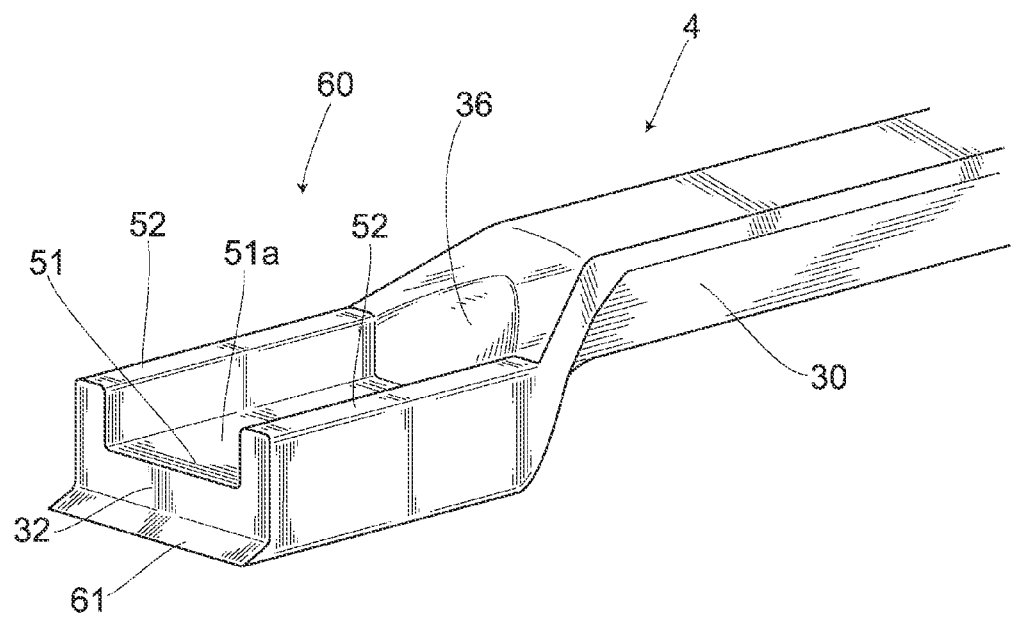
FIG. 8 is a view showing another modified example of a plunger of the same as above.
Figure 9A:
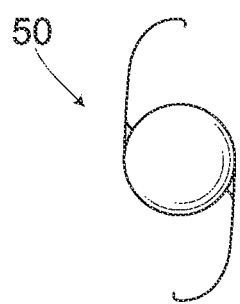
FIG. 9A is a plan view of an intraocular lens having filament-shaped supporting portions.
Figure 9B:
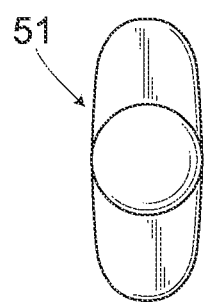
FIG. 9B is a plan view of an intraocular lens having a plate-like supporting portion.
Figure 9C:
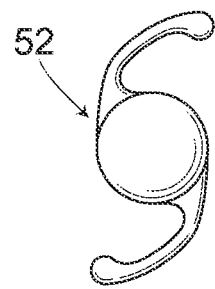
FIG. 9C is a plan view of an intraocular lens having thin plate-like supporting portions.

In addition, the plunger 60 shown in FIG. 8 is provided with a scooping face 61 at the lens contact portion 32 on the pushing portion 50 shown in FIG. 7. Providing such a scooping face 61 at the lens contact portion 32 can prevent the distal end of the plunger 4 from running on the optic 6 in the process of movement of the intraocular lens 5. In this modified example, the same effect as the above embodiment can be obtained by providing the pushing portion 50.

The present invention is not limited to the embodiment described above, and various modifications can be made thereto within the scope of the present invention. For example, in the above-mentioned embodiment, the transition part of the main body has a mortar shape tapering toward the distal end, and the intraocular lens 5 is folded into a small size by passing through the transition part. The present invention, however, is not limited to this embodiment, but applies to the main body having a simple cylindrical transition part.

According to the above-mentioned embodiment, the supporting portions are thin plates. The present invention, however, is not limited to this embodiment, but applies to an intraocular lens having thin filament-shaped supporting portions.

The invention claimed is:

1. A method of operating an insertion device including a main body, a nozzle, and a tapered transition portion proximal of the nozzle, the method comprising the steps of:
   applying force to an intraocular lens, located within the main body and having an optic, a leading loop haptic with a fixed end at the optic and a free end, and a trailing loop haptic with a fixed end at the optic and a free end, with a plunger, including a distal portion with a lens contact surface and a slot that extends proximally from the lens contact surface, in such a manner that a portion of the trailing loop haptic is located within the slot while being bent toward the nozzle by the distal portion and the free end of the trailing loop haptic points toward the nozzle; and
   pushing the intraocular lens into the nozzle with the plunger.

2. A method as claimed in claim 1, wherein
   the trailing loop haptic is in an unbent state prior to force being applied with the plunger.

3. A method as claimed in claim 1, wherein
   the main body and nozzle of the insertion device define a lens advancing axis; and
   the free end of the trailing loop haptic is located on the lens advancing axis when pointing toward the nozzle.

4. A method as claimed in claim 1, wherein
   the main body and nozzle of the insertion device define a lens advancing axis; and
   the distal portion with the lens contact surface and the slot has an outer surface that defines a non-circular shape in a cross-section that is perpendicular to the lens advancing axis.

5. A method as claimed in claim 1, wherein the trailing and leading loop haptics comprise filament shaped loop haptics.

6. A method as claimed in claim 1, wherein the trailing and leading loop haptics comprise thin plate loop haptics.

7. A method as claimed in claim 1, wherein the distal portion of the plunger includes a scoop projecting from the lens contact surface.

8. A method as claimed in claim 1, further comprising the step of:
folding the optic prior to applying force to the intraocular lens with a plunger.

9. A method as claimed in claim 8, wherein
the main body and nozzle of the insertion device are part of a cartridge;
the method further comprises the step of placing the intraocular lens with the folded optic into the cartridge prior to applying force to the intraocular lens with a plunger.

10. A method as claimed in claim 1, wherein
the main body and nozzle of the insertion device define a lens advancing axis; and
the slot comprises an elongate slot that is located on the lens advancing axis.

11. A method as claimed in claim 1, wherein
at least a portion of the trailing haptic is bent into a U-shape when the trailing loop haptic is located within the slot and the free end of the trailing loop haptic points toward the nozzle.

12. A method of operating an insertion device including a main body and a nozzle, the method comprising the step of:
applying force to an intraocular lens, located within the main body and having an optic, a leading loop haptic with a fixed end at the optic and a free end, and a trailing loop haptic with a fixed end at the optic and a free end, with a plunger, including a distal portion with a lens contact surface and an elongate slot that extends proximally from the lens contact surface, in such a manner that a portion of the trailing loop haptic is located within the elongate slot while being bent toward the nozzle by the distal portion and the free end of the trailing loop haptic points toward the nozzle prior to the lens contact surface contacting the optic.

13. A method as claimed in claim 12, further comprising the step of:
engaging the optic with the lens contact surface after the trailing loop haptic is located within the elongate slot and the free end of the trailing loop haptic points toward the nozzle.

* * * * *